(12) United States Patent
Chin et al.

(10) Patent No.: US 11,207,425 B2
(45) Date of Patent: Dec. 28, 2021

(54) GUIDE RNA MOLECULE AND METHOD FOR TREATING CANCER

(71) Applicant: City University of Hong Kong, Kowloon (HK)

(72) Inventors: Yuet Ming Rebecca Chin, Kowloon Tong (HK); Xin Wang, Kowloon (HK); Jianyang Hu, Kowloon (HK)

(73) Assignee: City University of Hong Kong, Kowloon (HK)

( * ) Notice: Subject to any disclaimer, the term of this patent is extended or adjusted under 35 U.S.C. 154(b) by 498 days.

(21) Appl. No.: 16/145,616

(22) Filed: Sep. 28, 2018

(65) Prior Publication Data

US 2020/0101172 A1 Apr. 2, 2020

(51) Int. Cl.
| | | |
|---|---|---|
| *C12N 15/11* | (2006.01) | |
| *A61K 48/00* | (2006.01) | |
| *A61P 35/00* | (2006.01) | |
| *C12N 15/86* | (2006.01) | |
| *C12N 15/10* | (2006.01) | |

(52) U.S. Cl.
CPC ............ *A61K 48/005* (2013.01); *A61P 35/00* (2018.01); *C12N 15/102* (2013.01); *C12N 15/86* (2013.01); *C12N 2310/20* (2017.05)

(58) Field of Classification Search
CPC ..... C12N 9/22; C12N 15/113; C12N 2310/20
See application file for complete search history.

(56) References Cited

U.S. PATENT DOCUMENTS

| | | | | |
|---|---|---|---|---|
| 2014/0234972 A1* | 8/2014 | Zhang | ................. | C12N 9/22 435/456 |
| 2015/0232883 A1* | 8/2015 | Dahlman | ............. | C12N 15/102 435/462 |
| 2016/0074535 A1* | 3/2016 | Ranganathan | ....... | C12N 15/907 514/44 R |

OTHER PUBLICATIONS

Park et al., CRISPR/Cas9 allows efficient and complete knock-in of a destabilization domain-tagged essential protein in a human cell line, allowing rapid knockdown of protein function, PLOS One, vol. 9, issue 4:e95101, pp. 1-8. (Year: 2014).*

* cited by examiner

*Primary Examiner* — Dana H Shin
(74) *Attorney, Agent, or Firm* — Renner Kenner Greive Bobak Taylor & Weber

(57) ABSTRACT

A gRNA molecule includes a first domain complementary to at least a portion of TCOF1 gene, and a second domain for binding with Cas9 protein, and a kit includes the gRNA molecule. A method of treating a subject suffering from a cancer associated with an elevated expression of TCOF1 gene includes the step of administering an effective amount of a first recombinant vector comprising the gRNA molecule of the invention to the subject. A method of inhibiting the expression of TCOF1 gene in cancer cells associated with an elevated expression of TCOF1 gene includes contacting the cancer cells with a first recombinant vector, wherein the first recombinant vector comprises a gRNA molecule comprising a first domain complementary to at least a portion of TCOF1 gene and a second domain binding with Cas9 protein.

9 Claims, 10 Drawing Sheets

Specification includes a Sequence Listing.

| Brest tumor cell line | ER | PR | Her2 | p53 status | TNBC subtype |
|---|---|---|---|---|---|
| HCC1806 | - | - | - | - | Basal-like |
| MDA-MB-468 | - | - | - | MUT | Basal-like |
| HCC70 | - | - | - | MUT | Basal-like |
| MCF-10-DCIS | - | - | - | WT | Basal-like |
| BT549 | - | - | - | MUT | Mesenchymal-like |
| MDA-MB-231 | - | - | - | MUT | Mesenchymal-like |
| T47D | + | + | + | MUT | |
| ZR-75-1 | + | + | + | WT | |
| MCF7 | + | + | + | WT | |

Fig. 5

SEQUENCE LISTING

<160> NUMBER OF SEQ ID NOS: 2

<210> SEQ ID NO 1
<211> LENGTH: 20
<212> TYPE: RNA
<213> ORGANISM: Artificial Sequence
<220> FEATURE:
<223> OTHER INFORMATION: Synthesized

<400> SEQUENCE: 1
ggggauggug ucagcgggcc         20

```
<210> SEQ ID NO 2
<211> LENGTH: 20
<212> TYPE: RNA
<213> ORGANISM: Artificial Sequence
<220> FEATURE:
<223> OTHER INFORMATION: Synthesized

<400> SEQUENCE: 2
gggccggcgc cuuuccccaa                                               20
```

GUIDE RNA MOLECULE AND METHOD FOR TREATING CANCER

SEQUENCE LISTING

The Sequence Listing file entitled "sequencelisting" having a size of 4,096 bytes and a creation date of Sep. 28, 2018 that was filed with the patent application is incorporated herein by reference in its entirety.

TECHNICAL FIELD

The present invention relates to a guide RNA molecule and its medical use in treatment of cancer. Particularly, but not exclusively, the invention relates to a gRNA molecule useful for gene-editing technology and a method of treating a subject suffering from breast cancer.

BACKGROUND OF THE INVENTION

Breast cancer is the most common cancer affecting women worldwide. Despite recent improvement in mortality of breast cancer, this disease remains the second most common cause of death of women. Breast cancer has been categorized into three major subtypes: luminal, HER2+/ER−, and basal-like. About 70% of basal-like tumors are triple-negative tumors which lack three most common types of receptors—receptors for estrogen, progesterone and HER-2/neu. This type of breast cancer is triple-negative breast cancer (TNBC). TNBC cannot be treated with therapies or drugs that work by targeting estrogen, progesterone and HER-2. Chemotherapy, usually with high toxicity, is the main treatment option for basal-like and TNBC, and there are few options exist outside of chemotherapy. Accordingly, there is a strong need to devise new treatment options for treating TNBC and/or alleviating the symptoms associated with TNBC. It would generally be desirable to have the treatment options with reduced risk for side effects.

SUMMARY OF THE INVENTION

In a first aspect, the invention provides a guide RNA (gRNA) molecule comprising a first domain complementary to at least a portion of TCOF1 gene, and a second domain for binding with Cas9 protein. Preferably, the TCOF1 gene is derived from human. In an embodiment, the gRNA molecule comprises a sequence of SEQ ID NO:1, SEQ ID NO:2 or a homologue thereof.

In a second aspect, the invention pertains to kit comprising the gRNA molecule. In an embodiment, the kit further comprises an inducible promoter for inducing the expression of the gRNA in a cell. Preferably, the gRNA molecule comprises a sequence of SEQ ID NO:1, SEQ ID NO:2 or a homologue thereof.

In a third aspect, the present invention pertains to a method of treating a subject suffering from a cancer associated with an elevated expression of TCOF1 gene, the method comprising the step of administering an effective amount of a first recombinant vector comprising a gRNA molecule to the subject, wherein the gRNA molecule comprises a first domain complementary to at least a portion of TCOF1 gene, and a second domain for binding with Cas9 protein.

Further, in a fourth aspect, the present invention provides a method of inhibiting the expression of TCOF1 gene in cancer cells associated with an elevated expression of TCOF1 gene, the method comprising the step of contacting the cancer cells with a first recombinant vector, wherein the first recombinant vector comprises a gRNA molecule comprising a first domain complementary to at least a portion of TCOF1 gene and a second domain binding with Cas9 protein.

Accordingly, the invention provides a novel and effective approach for treating disease associated with abnormal expression of TCOF1 gene in particular triple negative breast cancer. The inventors unexpectedly found that TCOF1 gene is associated with the growth and/or progression of the cancer cells in particular triple negative breast cancer having an elevated expression of TCOF1 gene. The provision of the first recombinant vector containing the gRNA of the invention and the second recombinant vector encoding Cas9 protein establishes a gene-editing system in a cell. The administration of inducible promoter induces the transcription of the gRNA, and the production of Cas9 protein which is guided by the gRNA to cut the target gene, i.e. TCOF1 gene, at a specific location. The target gene will then recover from the alternation and the resultant change in the genome causes the gene to silence or have low level of expression. Accordingly, the overexpression of TCOF1 gene in the cell is inhibited. The application of the gRNA molecule in combination with the induction caused by the inducible promoter allows efficient inhibition of abnormal expression of TCOF1 gene and therefore it is believe to be effective in treating and/or preventing diseases associated with abnormal expression of TCOF1 gene. This present invention provides an alternative to treat TNBC via a targeted therapy. The gRNA and the related kit comprising it are also parts of the invention.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 5 shows a table listing the characteristics of each breast tumor lines.

DETAILED DESCRIPTION OF THE EMBODIMENTS

Figure 1A:
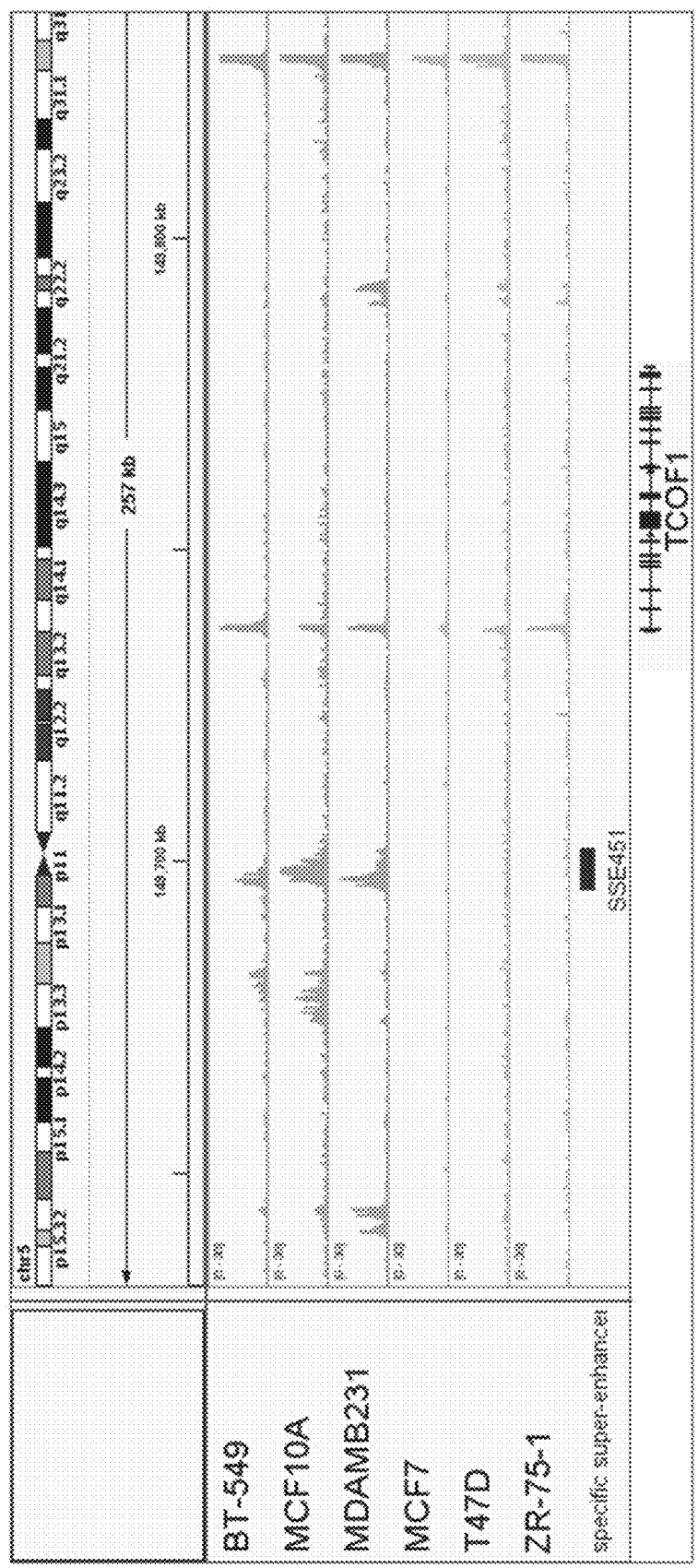
FIG. 1a shows H3K27Ac patterns in TNBC and luminal breast cells lines including BT-549, MCF10A, MDAMB231, MCF7, T47D and ZR-75-1 cell lines.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention in the first aspect provides a gRNA molecule comprising a first domain complementary to at least a portion of TCOF1 gene, and a second domain for binding with Cas9 protein. gRNA molecule refers to RNA that guides the addition or deletion of residues on a target gene. Preferably, the gRNA molecule has a first domain, i.e. a portion of sequence, complementary to at least a portion of a target gene. The first domain is part of an RNA molecule and therefore comprises the base uracil (U), while any DNA encoding the gRNA molecule comprises the base thymine (T). The "target gene" as used herein refers to a gene of interest and particularly refers to TCOF1 gene in this invention. Preferably, the TCOF1 gene is derived from a mammal such as a human or an animal, more preferably the TCOF1 gene is derived from human. The TCOF1 gene refers to a gene encoding a protein Treacle Ribosome Biogenesis Factor 1, a nucleolar phosphoprotein, which is found to have effect in ribosome biogenesis. With the provision of the first domain as described above, the gRNA molecule is capable of selectively binding to the target gene.

In an embodiment, the first domain of gRNA molecule is complementary to exon1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, or exon 27 of genomic DNA encoding human TCOF1 and wherein the first domain is configured to introduce a frameshift mutation or a stop codon.

The gRNA molecule further has a second domain for binding with Cas9 protein. The provision of the second domain on the gRNA molecule allows Cas9 protein to locate the specific cutting position on the target gene and cuts the double strands of the target gene. This is thus advantageous in that the gRNA molecule of the present invention allows gene editing in a cell such as a cancer cell to alter the expression of the target gene.

Preferably, the gRNA molecule has a length of from 15 to 20 nucleotides, 18 to 20 nucleotides, 19 or 20 nucleotides.

In an embodiment, the gRNA molecule comprises a sequence of SEQ ID NO: 1 or SEQ ID NO:2 or a homologue thereof. The term "homologue" used herein refers to nucleotides having a sequence identity of at least 50%, at least 60%, at least 70%, at least 80%, at least 90% or at least 95% to the gRNA molecules according to the present invention. In an embodiment, the homologue of the gRNA molecule has at least 90%, 91%, 92%, 93%, 94%, 95%, 96%, 97%, 98%, or 99% overall sequence identity to the gRNA molecule. In a particular embodiment, the gRNA molecule consists of a sequence of SEQ ID NO:1, SEQ ID NO:2, or a homologue thereof.

The gRNA molecule of the present invention is preferably provided in a recombinant vector. The term "recombinant vector" as used herein refers to a vector such as a plasmid that contains a foreign nucleic acid introduced therein. The recombinant vector is then inserted into a cell for example through infection. The transcription of the recombinant vector allows the transcription of the foreign nucleic acid and thus may result in expression of the foreign nucleic acid. A person skilled in the art would appreciate suitable methods for introducing the recombinant vector into a cell for infection.

Accordingly, the present invention also provides a recombinant vector comprising the gRNA molecule as described above, as well as a kit comprising the recombinant vector containing the gRNA molecule as described above. The kit is suitable for treating diseases associated with the TCOF1 gene in particular associated with abnormal expression of TCOF1 gene, or inhibiting the expression of the TCOF1 gene in a cell or a subject.

In an embodiment, the kit comprises first recombinant vector which contains a gRNA molecule. The gRNA molecule comprises a sequence of SEQ ID NO:1, SEQ ID NO:2 or a homologue thereof. Particularly, the gRNA molecule may consist of a sequence of SEQ ID NO:1, SEQ ID:2 or a homologue thereof. The first recombinant vector may be prepared by ligating the gRNA molecule of the invention to a vector. The vector may be commercially available vectors or prepared and synthesized in laboratory. A person skilled in the art would appreciate the appropriate vector for carrying the gRNA molecule of the invention, and the conditions for inserting the gRNA molecule into the vector.

Preferably, the kit further comprises a second recombinant vector which contains a sequence for encoding Cas protein in particular Cas9 protein. When the second recombinant vector is transfected into a cell, the transcription of the second recombinant vector allows production of the Cas9 protein. The produced Cas9 protein is then capable of binding to the second domain of the gRNA molecule present in the same cell for gene-editing process. The co-presence of the first recombinant vector and the second recombinant vector in the same cell provides suitable conditions for altering the target gene in that particular cell.

Preferably, the kit further comprises an inducible promoter. The term "inducible promoter" as used herein refers to a chemical or molecule that can control gene expression of a particular gene, in particular inducing a target gene to express in a system. In an embodiment of the present invention, the inducible promoter is a tetracycline including tetracycline-type antibiotic or its derivative which is capable of inducing the expression of a target gene. It is particularly advantageous in a tetracycline-dependent system in particular tetracycline-dependent CRISPR/Cas system. In a tetracycline-dependent system, a Tet response element (TRE) is recognized by the tetracycline repressor (tetR). When a tetracycline is present, tetR will bind to the tetracycline and not to the TRE, permitting transcription. Preferably, the tetracycline is selected from doxycycline, oxytetracycline, chlortetracycline, anhydrotetracycline or derivative thereof. In a particular embodiment, the inducible promoter for inducing the expression of the gRNA molecule is doxycycline.

It would be appreciated that the kit may further comprise other suitable excipients such as buffers or reagents for facilitating the application of the kit. Preferably, the kit may be applied in various applications such as medical applications including therapies and diagnosis, researches and the like. Accordingly, the gRNA molecule and the kit of the present invention may be used in the preparation of medicament for treatment and/or in the preparation of an agent for research study.

In a further aspect, the present invention provides a method of treating a subject suffering from cancer. The method comprises a step of administering an effective amount of a first recombinant vector as described above to said subject. Preferably, the cancer is associated with an elevated expression of TCOF1 gene. The first recombinant vector administered according to the present invention is as described above, and may be modified or artificially synthesized according to the sequences and steps disclosed in the present invention. In particular, the first recombinant vector comprises a first domain complementary to at least a portion of TCOF1 gene, and a second domain for binding with Cas9 protein as described above.

In an embodiment the gRNA molecule has a length of from 15 to 20 nucleotides, 18 to 20 nucleotides, 19 or 20 nucleotides. Preferably, the gRNA molecule comprises a sequence selected from SEQ ID NO:1, SEQ ID NO:2 or a homologue thereof. In a particular embodiment, the gRNA molecule consists of SEQ ID NO: 1, SEQ ID NO:2 or a homologue thereof.

The term "cancer" describes a physiological condition in subjects in which a population of cells are characterized by unregulated malignant (cancerous) cell growth. Preferably, the cancer to be treated is associated with abnormal expression of TCOF1 gene, preferably an elevated expression of TCOF1 gene as compared to normal cells in a healthy subject. In particular, the cancer is breast cancer. More preferably, the cancer is a triple negative breast cancer (TNBC). The inventors unexpected found that the breast cancer is highly associated with abnormal expression of TCOF1 gene, in particular TNBC, which are further discussed in detail in the Examples below.

It would be appreciated that the gRNA molecules of the present invention are also effective in treating diseases associated with TCOF1 gene in particular those related to elevated expression of TCOF1 gene.

In the step of administering an effective amount of a first recombinant vector to the subject suffering from a cancer, the first recombinant vector may be provided in the form of pharmaceutical composition for administration via various routes. The term "subject" used herein refers to a living organism and can include but is not limited to a human and an animal. The subject is preferably a mammal, preferably a human. The first recombinant vector may be administered through injection to the subject, preferably a human. The term injection encompasses intravenous, intramuscular, subcutaneous and intradermal administration. In an embodiment, the first recombinant vector of the present invention is administered together with suitable excipient(s) to the subject through intravenous injection.

The expression "effective amount" generally denotes an amount sufficient to produce therapeutically desirable results, wherein the exact nature of the result varies depending on the specific condition which is treated. In this invention, cancer is the condition to be treated and therefore the result is usually an inhibition or suppression of the growth or proliferation of cancer cells, a reduction of cancerous cells or the amelioration of symptoms related to the cancer cells, in particular inhibition of the proliferation of the cancer cells or induction of cell death.

The effective amount of the first recombinant vector of the present invention may depend on the species, body weight, age and individual conditions of the subject and can be determined by standard procedures such as with cell cultures or experimental animals.

Preferably, the method further comprises a step of administering a second recombinant vector comprising a sequence encoding Cas9 protein as described above to the subject. The second recombinant vector is administered to the subject before, after or simultaneously with the first recombinant vector. In an embodiment, the second recombinant vector is administered after or simultaneously with the first recombinant vector; or the second recombinant vector is administered after the administration of the first recombinant vector. As described above, the transcription of the second recombinant vector allows production of Cas9 protein which can bind to the gRNA molecule of the present invention and perform gene-editing process.

In a particular embodiment, the method further comprises a step of administering an inducible promoter as described above to the subject after the administration of the first recombinant vector, or after the administration of the first and second recombinant vector. The inducible promoter is preferably a tetracycline selected from doxycycline, oxytetracycline, chlortetracycline, anhydrotetracycline or derivative thereof. The inducible promoter acts to induce the expression of the gRNA molecules in the subject.

In another aspect, there is provided a method of inhibiting the expression of TCOF1 gene in cancer cells in particular cancer cells associated with elevated expression of TCOF1 gene. The inhibition of the expression of TCOF1 gene may results in reduction of growth or proliferation of cancer cells as defined above. The method comprises the step of contacting the cancer cells with a first recombinant vector as described above, i.e. the first recombinant vector comprises a gRNA molecule of the present invention. The gRNA molecule comprises a first domain complementary to at least a portion of TCOF1 gene and a second domain binding with Cas9 protein. Preferably, the gRNA molecule comprises a sequence selected from SEQ ID NO:1, SEQ ID NO:2 or a homologue thereof.

In an embodiment, the method further comprises the step of contacting the cancer cells with a second recombinant vector as described above before, after or simultaneously with the first recombinant vector. The second recombinant vector preferably comprises a sequence encoding the Cas9 protein.

The method further comprises the step of incubating the cancer cells in a mixture comprising an inducible promoter as defined above, after contacting with the first recombinant vector, or after contacting with the first and second recombinant vector.

Preferably, the cancer cells are associated with abnormal expression of TCOF1 gene, preferably an elevated expression of TCOF1 gene as compared to normal healthy cells. In particular, the cancer cells are breast cancer cells. More preferably, the cancer cells are triple negative breast cancer cells.

Accordingly, the invention provides a novel and effective approach for treating disease associated with abnormal expression of TCOF1 gene in particular triple negative breast cancer. The inventors unexpectedly found that TCOF1 gene is associated with the growth and/or progression of the cancer cells in particular triple negative breast cancer having an elevated expression of TCOF1 gene and that the inhibition of the TCOF1 gene can significantly reduce the cell proliferation of cancer cells. The application of the gRNA molecule in combination with the induction caused by the inducible promoter allows efficient inhibition of abnormal expression of TCOF1 gene and therefore is believe to be effective in treating and/or preventing diseases associated with abnormal expression of TCOF1 gene. This present invention provides an alternative to treat TNBC via a targeted therapy.

The invention is now described in the following non-limiting examples.

EXAMPLES

Example 1

Determination of the Correlation Between Breast Cancer and TCOF1 Gene

The inventors determined the correlation between breast cancer and TCOF1 gene.

TCOF1 gene refers to a gene encoding TCOF1 which refers to Treacle Ribosome Biogenesis Factor 1, a nucleolar phosphoprotein, having an important role in ribosome biogenesis. Haploinsufficiency of TCOF1 results in Teacher Collins syndrome (TCS), one of the most severe congenital disorder of craniofacial development, highlighting its importance in cell proliferation and growth at the developmental stage.

Figure 1B:
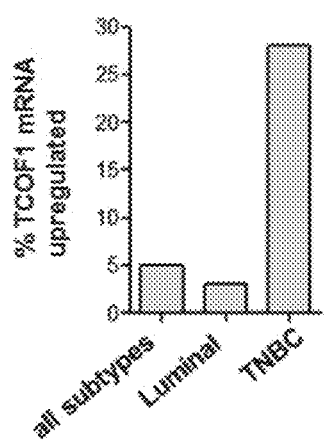
FIG. 1b shows a bar graph depicting the percentage of breast tumors in particular luminal and TNBC breast tumors having TCOF1 mRNA up-regulation.

The inventors unexpectedly found that TCOF1 gene is associated with breast cancer in particular triple negative breast cancer. The inventors generated bioinformatics data on H3K27Ac patterns in TNBC and luminal breast cells lines including BT-549, MCF10A, MDAMB231, MCF7, T47D and ZR-75-1 cell lines, as shown in FIG. 1a. The patterns reveal a TNBC-specific super-enhancer at TCOF1 proximal enhancer region. Then, the inventors analyzed clinically annotated breast cancer datasets (n=405) from the Cancer Genome Atlas and found that TCOF1 mRNA is up-regulated in 3% luminal breast tumors, its expression is significantly higher in 28% of TNBC cells, as shown in FIG. 1b.

Figure 1C:
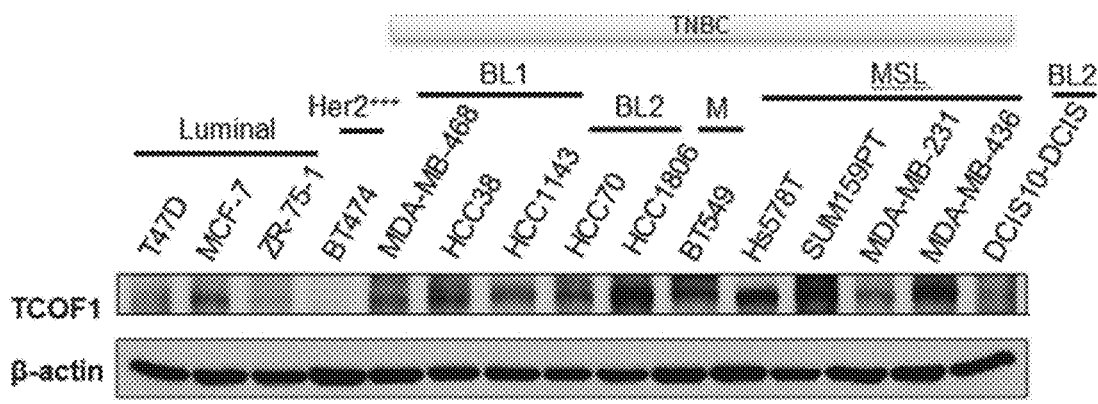
FIG. 1c shows an immunoblot pattern demonstrating the expression of TCOF1 in various breast cancer cell lines, wherein "BL1" denotes basal-like cancer cells 1, "BL2" denotes basal-like cancer cells 2, "M" denotes mesenchymal-like cancer cells, "MSL" denotes mesenchymal stem-like cancer cells.

Referring to FIG. 1c, the inventors also carried out immunoblot to determine the expression of TCOF1 in various breast cancer cell lines and found that the protein expression level of TCOF1 is higher in TNBC lines as compared to luminal or Her2-overexpressed cell lines. The results are in line with the bioinformatics data analysis in FIG. 1a and suggest that TCOF1 is regulated by super-enhancers enriched in TNBC cells. In the immunoblot analysis, non-TNBC cell lines (T47D, MCF-7, ZR-75-1), TNBC cell lines (MDA-MB-468, HCC38, HCC1143, HCC70, HCC1806, BT549, Hs578T, SUM159PT, MDA-MB-231, MDA-MB436) and MCF10-DCIS cell lines were seeded to 10-cm plates, when cells reached about 70% confluency, cells were harvested for immunoblotting to detect the TCOF1 expression, β-actin as a loading control. Anti-TCOF1 antibody (sigma #HPA038237) and anti-β-actin (CST #3700S) were used.

Figure 1D:
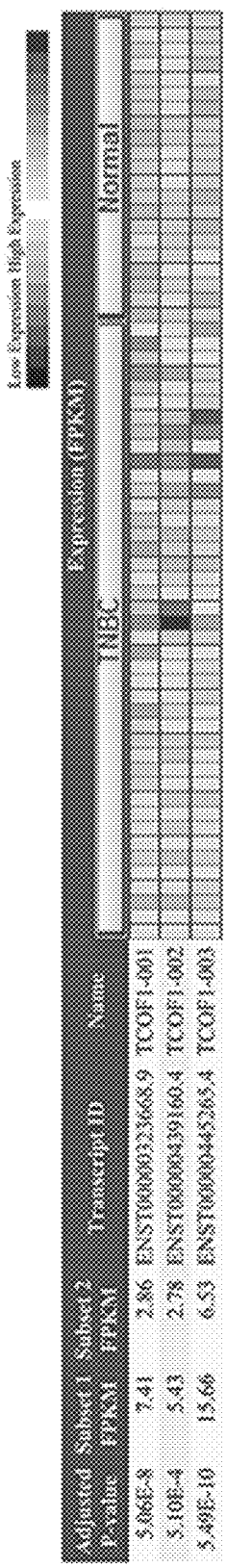
FIG. 1d is a plot showing bioinformatics data of mRNA expression level of TCOF1 transcript 1 to 3 in normal cells and TNBC tumors, wherein the data are generated based on RNA-sequence data from Cancer RNA-seq Nexus Database.
Figure 1E:
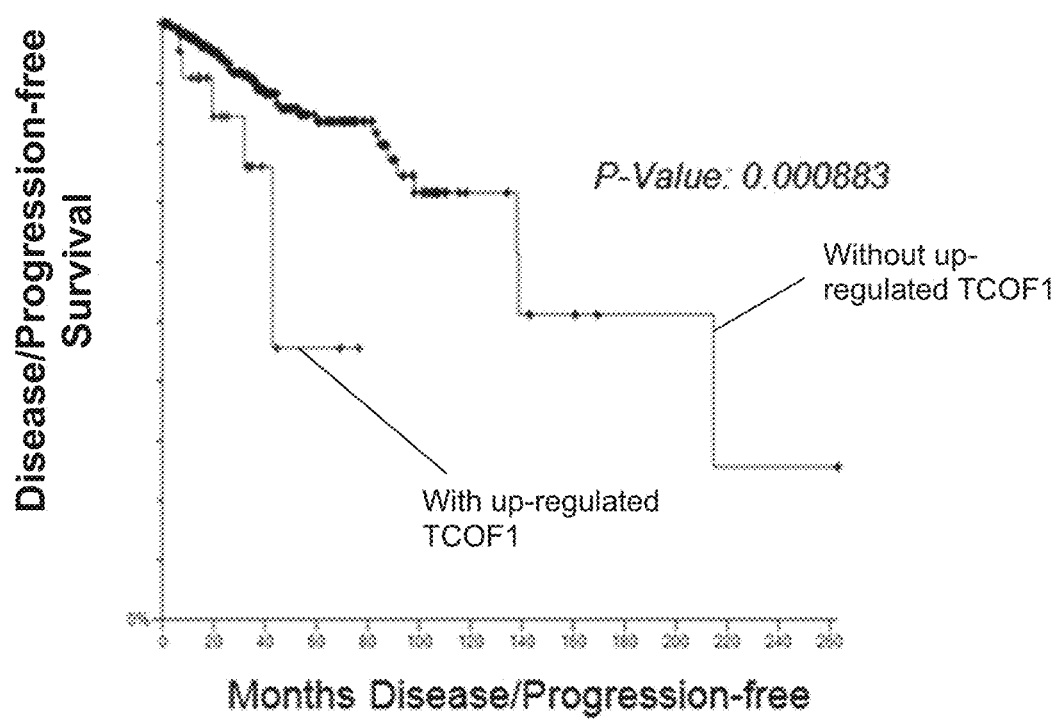
FIG. 1e is a plot generated based on data obtained from TCGA database via cBioportal and it shows the progression-free survival rate of breast cancer patients with or without TCOF1 overexpression over months.

Furthermore, FIG. 1d shows a plot with bioinformatics data of mRNA expression level of TCOF1 transcript 1 to 3 in normal cells and TNBC tumors, wherein the data are generated based on RNA-sequence data from Cancer RNA-seq Nexus Database. In particular, mRNA level of TCOF1 transcript1-3 in TNBC tumors are significantly higher than those in normal tissue samples that were adjacent to TNBC primary tumors, i.e. TCOF1 is minimally expressed in normal breast tissues. Based on the data obtained from TCGA database, it was found that the overexpression of TCOF1 is a predictor of poor survival in breast cancer patients as shown in FIG. 1e.

In short, breast cancer in particular triple negative breast cancer is associated with abnormal expression of TCOF1 gene. Accordingly, TCOF1 is a potential target for treating breast cancer in particular breast cancer associated with abnormal expression of TCOF1 gene or abnormal protein level of TCOF1.

Example 2A

Preparation of the First Recombinant Vector and the Second Recombinant Vector

The inventors then developed a method to inhibit the elevated expression of TCOF1 gene in cells by making use of gene-editing technology in particular CRISPR/Cas9 technology. In general, Cas9 enzyme acts as molecular scissors to cut DNA at a specific location. The cutting location on the genome is specified by the gRNA sequence. Once the DNA is cut, the cell's own natural repair machinery repairs the cut, i.e. a process that can disrupt a disease-causing gene, and prevent the expression of that particular gene.

To facilitate the inhibition, at least two recombinant vectors are prepared for containing a gRNA of the present invention and a Cas9 encoding gene, respectively. Fgh1tUTG (#70183) and FUcas9cherry (#70182) vectors from Addgene were used in the preparation.

The first recombinant vector is prepared to contain at least one gRNA molecule of the present invention. The preferred gRNA molecule is gRNA 1 having the sequence of SEQ ID NO:1, or gRNA 2 having the sequence of SEQ ID NO:2. In this example, gRNA 1 and gRNA 2 were designed and ligated to a lentiviral vector FgH1tUTG digested by BsmBI restriction enzyme (NEB, R0580S). In particular, in order to produce the first recombinant vector, psPAX2 packaging plasmid, VSVG envelop plasmid and FgH1tUTG-gRNA1/2 were co-transfected to HEK293T cells according to the following steps.
1. A DNA mastermix was prepared by mixing:
   0.6 ml serum-free, antibiotic-free DMEM;
   7.14 µg psPAX2 (Gag/Pol, 0.42 µg/µl);
   2.38 µg VSVG (Envelope, coat proteins, 0.1 µg/µl); and
   9 µg FgH1t vectors containing gRNA 1 or gRNA 2.
2. Polyethylenamine (PEI) was then added to 0.6 ml serum-free antibiotic-free DMEM.
3. The diluted PEI was then added to the diluted DNA gently at a ratio of DNA:PEI=1 µg:3 µg and mixed well with gentle agitation.
4. The supernatant was collected and incubated at room temperature for 15 min.
5. HEK293T cells were trypsinized by using 1 ml trypsin per 10 cm plate. Trypsin was inactivated with 9 ml/plate of 10% FBS/DMEM in the absence of penicillin and streptomycin. The number of cells was counted.
6. The cells collected were subject to centrifugation and the supernatant was removed. The cells were resuspended and the cell density was adjusted to $1 \times 10^7$ cells/8 ml.
7. 8 ml of collected cells were transferred to a 15-ml falcon tube and then mixed with the mixture prepared in step 4.
8. The mixture in step 7 was added to 10-cm plates and incubated in virus incubator for 48 h.
9. After 48 h of incubation, 0.45 µm filter was used to filter the mixture so as to obtain the lentivector particles, i.e. the first recombinant vector. 1 ml aliquots were prepared and stored at −80° C.

The second recombinant vector containing the sequence encoding Cas9 protein was prepared by the same procedure as described above but replacing 9 µg FgH1t vectors with 12.6 µg FUcas9-mcherry. In particular, psPAX2 packaging plasmid, VSVG envelop plasmid and FUcas9cherry were co-transfected to HEK293T cells.

Infection of Cells with the First and Second Recombinant Vectors

To establish HCC1806-Fgh1tUTG-FUCas9cherry and MDA-MB-468-Fgh1tUTG-FUCas9cherry cell lines. HCC1806 cells were maintained in RPMI-1640 medium supplemented with 10% tet-free fetal bovine serum. MDA-MB-468 cells were maintained in RPMI-1640 medium supplemented with 10% tet-free fetal bovine serum. HCC1806 and MDA-MB-468 cells were seeded to 6-cm plate, then cells were infected by the FgH1tUTG-gRNA1/2 lentivector particles and FUCas9cherry lentivector particles, sequentially, i.e. infected by the first and second recombinant vectors one by one. Since FgH1tUTG and FUCas9mcherry encode eGFP and mCherry protein respec-tively, the inventors performed Fluorescence Activated Cell Sorting (FACS) experiment to sort the cells with both eGFP and mCherry. Double positive cells were then collected and cultured with subsequent analysis.

Example 2B

Induction of the Gene Expression

The inventors then determined the effect of knocking out TCOF1 by use of an inducible promoter. In this example, doxycycline was used to induce the transcription of the gRNA molecule which has been infected in the cells so as to guide the Cas9 protein to cut the target sequence of TCOF1 gene. I.e. the Cas9 protein is expressed to cut the target TCOF1 gene at a location specified by the gRNA molecule. Accordingly, the cell will then automatically repair with an alternation in the expression of TCOF1 gene.

Figure 2:
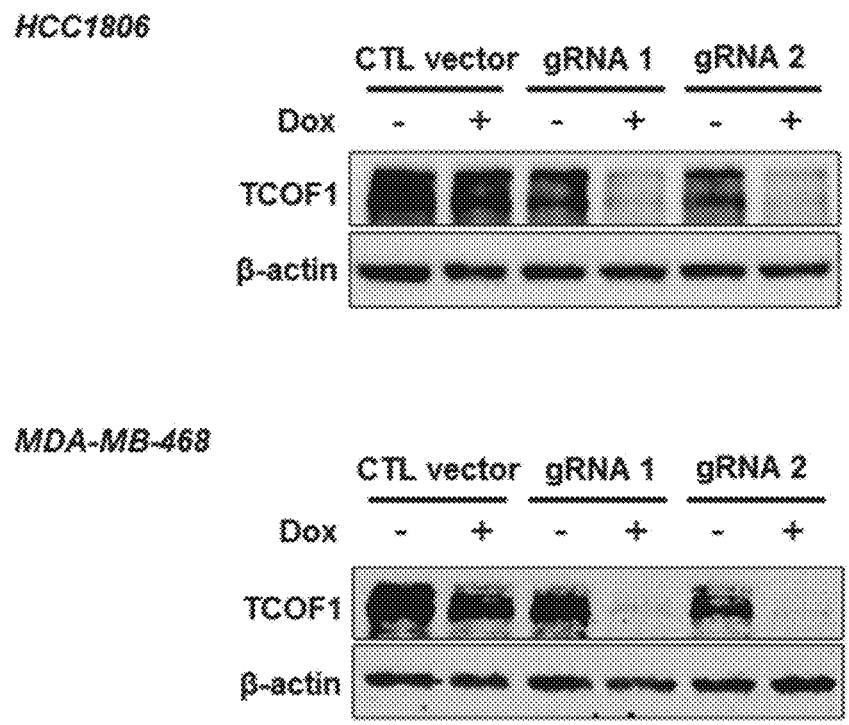
FIG. 2 shows immunoblot patterns demonstrating the expression level of TCOF1 gene in HCC1806 cells and MDA-MB-4468 cells which harbor the first gRNA (denoted as gRNA 1) or the second gRNA (denoted as gRNA 2) of the present invention after treatment of 100 ng/ml doxycycline (denoted as dox) for 7 days.

In this example, $1 \times 10^6$ cells were seeded to 10-cm plates treated with or without 100 ng/ml doxycycline for 7 days refreshing medium with or without 100 ng/ml doxycycline every 3 to 4 days. After doxycycline treatment, cells were harvested and TCOF1 expression was analyzed by immunoblotting. FIG. 2 shows immunoblot patterns demonstrating the expression level of TCOF1 gene in HCC1806 cells and MDA-MB-468 cells which harbor gRNA 1 or gRNA 2 of the present invention after treatment of 100 ng/ml doxycycline for 7 days. The results demonstrate that doxycycline is capable of inducing the transcription of the gRNA molecule of the present invention and the gRNA molecules are capable of inhibiting the expression of TCOF1 gene in cancer cells. The Tet-on CRISPR/Cas9 system of the present invention is useful to knock out TCOF1.

Example 3

Effect of the gRNA Molecule on In Vitro Cancer Cells

Figure 3A:
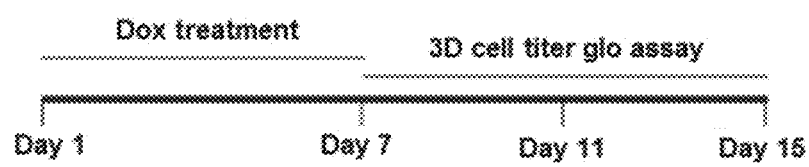
FIG. 3a is a schematic diagram showing the schedule of doxycycline treatment and 3D cell titer glo assay. In particular TCOF1 knockout in HCC1806 cells was induced by 100 ng/ml doxycycline treatment for 7 days, cells were then seeded and grown in 3D cultures, followed by 3D cell titer glo assay. Luminescence signal was captured on Day 7, Day 11 and Day 15.
Figure 3B:
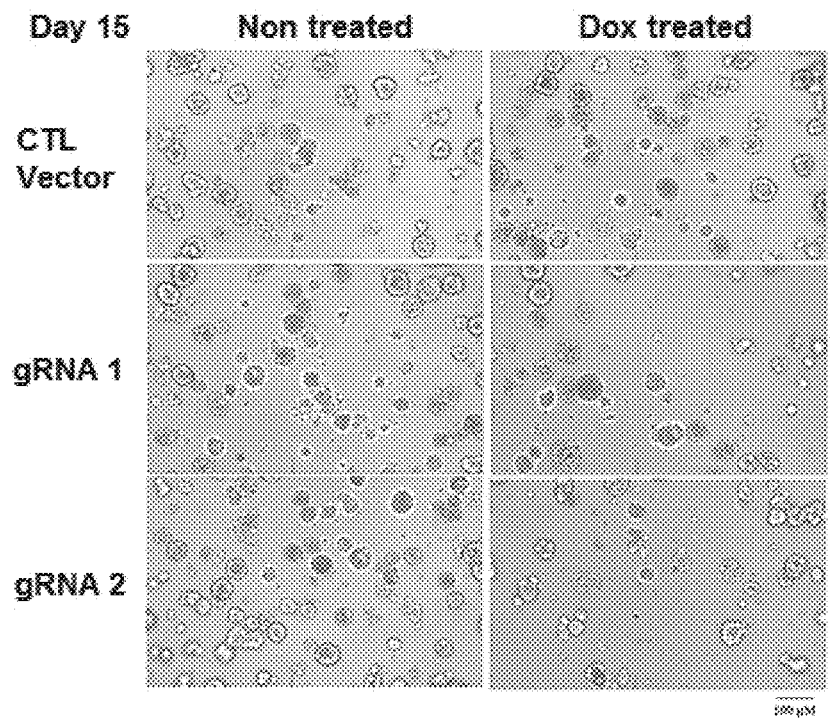
FIG. 3b shows representative phase-contrast images of gRNA 1- or gRNA 2-infected HCC1806 spheroids obtained from 3D cell titer glo assay on Day 15.

CellTiter-Glo 3D cell viability assay (Promega #G9682) was performed to determine spheroid growth of cancer cells infected as described in Example 2. Referring to FIG. 3a, it shows the schedule of doxycycline treatment and 3D cell titer glo assay. From day 1 to day 7, cells were treated with or without 100 ng/ml doxycycline. On day 7, 45 µl/well Matrigel (corning #354230) were pre-coated to 96-well white polystyrene microplate (corning #3610), followed by incubation in 37° C. for 30 min to solidify the Matrigel. Cells were resuspended in assay medium (10% tet-free FBS RPMI-1640 containing 2% Matrigel), then 1500 cells/well were seeded, assay medium was refreshed every 4 days. On day 15, pictures were captured using a phase-contrast microscope. With reference to FIG. 3b, although morphology of the cells did not change significantly, the spheroid density of HCC1806 cells pretreated with doxycycline was markedly decreased.

Figure 3C:
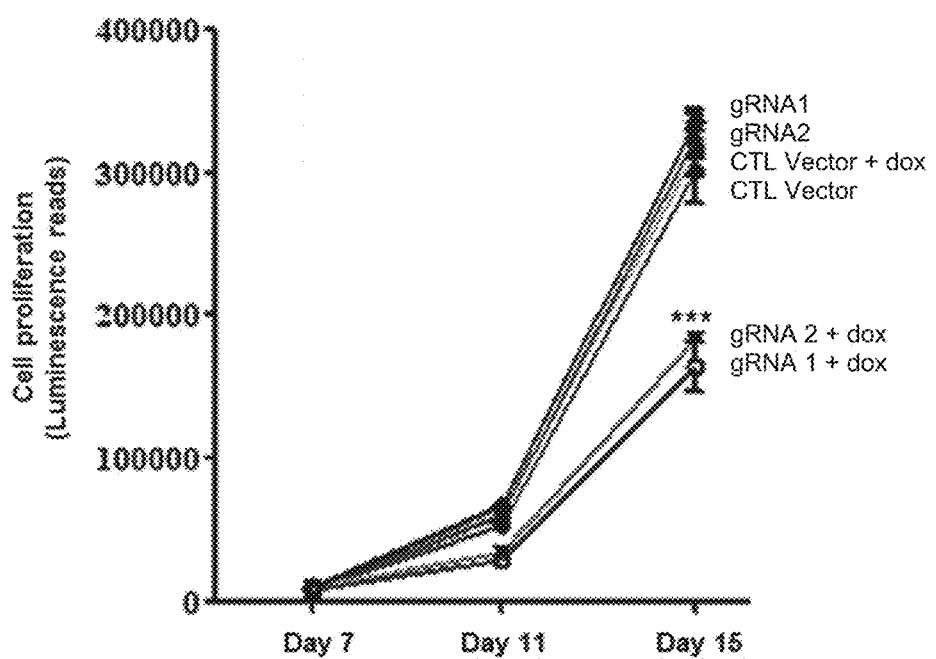
FIG. 3c is a plot showing the cell proliferation of gRNA 1- or gRNA 2-infected HCC1806 cells in 3D cell titer glo assay after treatments with or without dox, together with control groups, ***p<0.001.

On Day 7 (after cells were seeded), Day 11 and Day 15, 100 ul 3D CellTiter Glo reagent (Promega #G9682) was added to each well. The cells were incubated at room temperature for 15 min before subjecting to a multifunctional microplate reader (BioTek Synergy™ H1 Microplate Reader) for reading the chemiluminescence signal. Again, FIG. 3c demonstrates that TCOF1 knockout in HCC1806 cells with induction by doxycycline results in significant decrease in spheroid growth compared to non-dox treated cells.

Figure 4A:
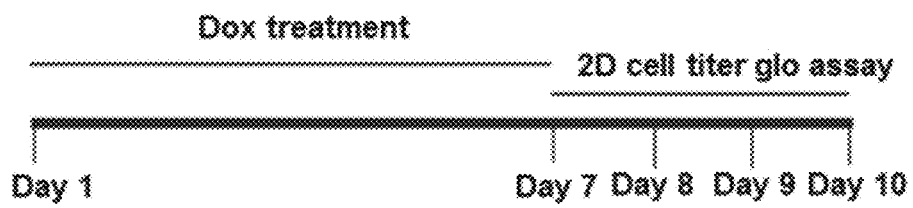
FIG. 4a is a schematic diagram showing the schedule of doxycycline treatment and 2D cell titer glo assay. In particular TCOF1 knockout in HCC1806 cells was induced by 100 ng/ml doxycycline treatment for 7 days, cells were then seeded and grown in 2D cultures, followed by 2D cell titer glo assay. Luminescence signal was captured on Day 7, Day 8, Day 9 and Day 10.
Figure 4B:
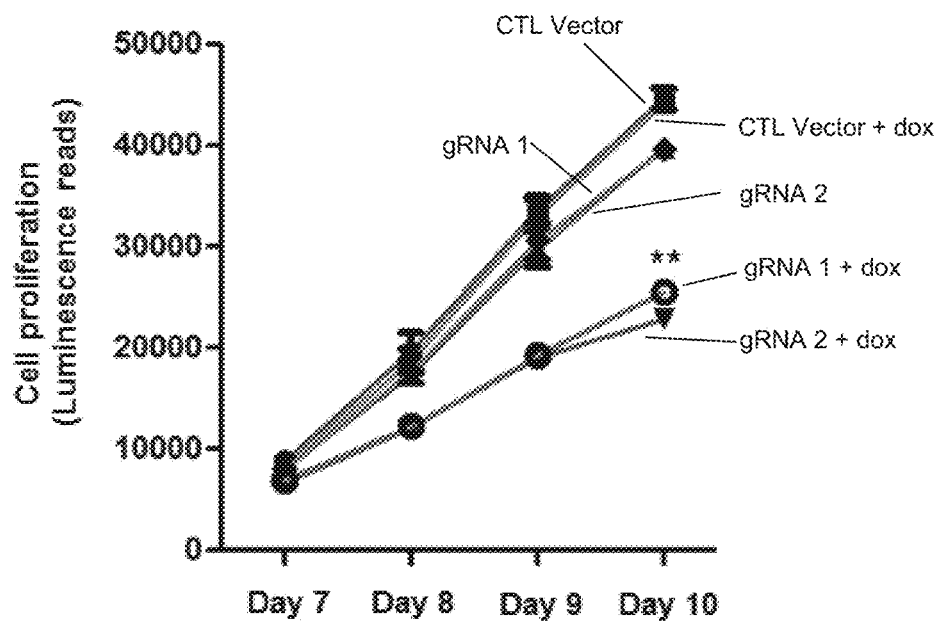
FIG. 4b is a plot showing the cell proliferation of gRNA 1- or gRNA 2-infected HCC1806 and MDA-MB-468 cells with or without doxycycline treatment compared to the control groups, in which the cell proliferation was determined by 2D cell titer glo assay, **p<0.01.
Figure 4C:
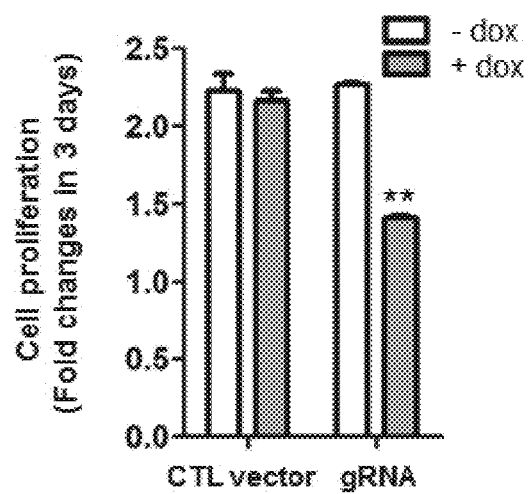
FIG. 4c is a plot showing the fold changes in cell proliferation of gRNA 1- or gRNA 2-infected HCC1806 and MDA-MB-468 cells with or without doxycycline treatment based on the results in FIG. 4b.

Further, FIG. 4a illustrates the schedule for performing the doxycycline treatment and 2D cell titer glo assay. From day 1 to day 7, HCC1806-FgH1tUTG(vector CTL)-FUCas9cherry, HCC1806-FgH1tUTG-gRNA1-FUCas9cherry and HCC1806-FgH1tUTG-gRNA2-FUCas9cherry cells were treated with or without 100 ng/ml doxycycline, while the medium with or without 100 ng/ml doxycycline was refreshed every 3 to 4 days. Cells were then detached from plates by trypsin and resuspended in 10% tet-free FBS RPMI-1640 medium, then 2000 cells/well were seeded to 96-well white polystyrene microplate (corning #3610). On day 10, 50 ul CellTiter Glo reagent (Promega #G7571) was added to each well. The cells were incubated at room temperature for 5 min before subjecting to a multifunctional microplate reader (BioTek Synergy™ H1 Microplate Reader) for reading the chemiluminescence signal. FIGS. 4b and 4c, respectively, shows that cells infected with the gRNA molecule of the present invention and induced by doxycycline have reduced cell proliferation compared to the control group having cells containing empty vector.

Figure 4D:
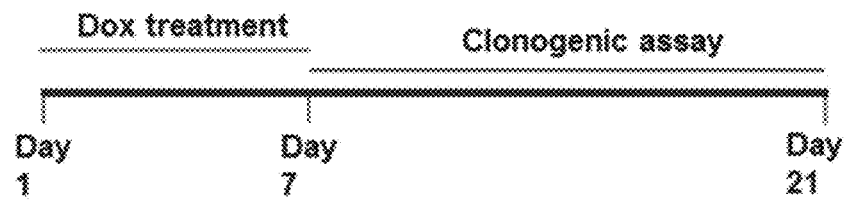
FIG. 4d is a schematic diagram showing the schedule of doxycycline treatment and clonogenic assay.
Figure 4E:
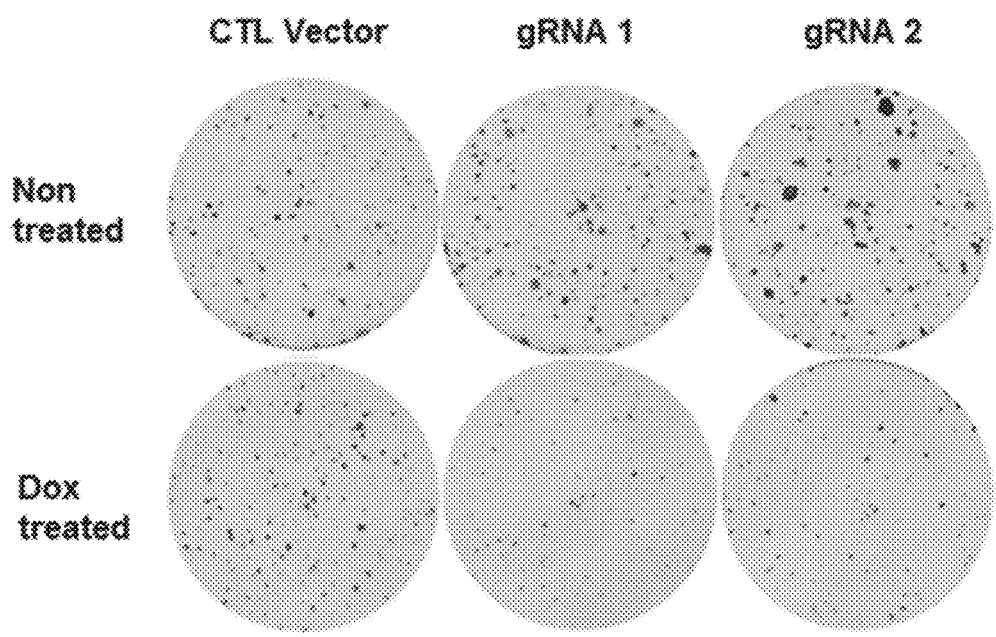
FIG. 4e shows microscopic images of gRNA 1- or gRNA 2-infected HCC1806 cells with or without doxycycline treatment. The images shows that the gRNA 1- or gRNA 2-infected cells inhibit has a reduced colony formation ability with doxycycline treatment.

Clonogenic assay was also performed to determine the colony formation ability of the infected cells. FIG. 4d demonstrates the schedule of doxycycline treatment and clonogenic assay. From day 1 to day 7, HCC1806-FgH1tUTG(vector CTL)-FUCas9cherry, HCC1806-FgH1tUTG-gRNA1-FUCas9cherry and HCC1806-FgH1tUTG-gRNA2-FUCas9cherry cells were treated with or without 100 ng/ml doxycycline, while the medium with or without 100 ng/ml doxycycline was refreshed every 3 to 4 days. On day 7, 1000 cells/well were seeded to 6-well plate, 10% tet-free FBS RPMI-1640 medium were refreshed every 4 days. Cells were cultured for 14 days, then fixed by 4% formaldehyde at room temperature for 10 min followed by 0.1% crystal violet (in ethanol) staining for about 20 min at room temperature. The plates were washed by PBS for 3 times to remove unstained crystal violet. Then the microscopic images of the cells were captured. As shown in FIG. 4E, the infected cells containing gRNA molecule of the present invention exhibit a significant decrease in the number of colony of cells after doxycycline treatment. In other words, the gRNA molecule of the present invention is useful to inhibit the growth and development of cancer cells in particular cancer cells associated with an elevated expression of TCOF1 gene.

Example 4

Effect of the gRNA Molecule in Animal Model 6-week-old female nude mice were purchased from Chinese University of Hong Kong. Mice were randomly grouped into 6 groups as indicated in FIG. 3d, i.e. a control group with empty vector, another control group with empty vector and treated with doxycycline, a gRNA 1 group without doxycycline treatment, a gRNA 1 group with doxycycline treatment, a gRNA 2 group without doxycycline treatment, and a gRNA 2 group with doxycycline treatment.

HCC1806-FgH1tUTG(vector CTL)-FUCas9cherry, HCC1806-FgH1tUTG-gRNA1-FUCas9cherry and HCC1806-FgH1tUTG-gRNA2-FUCas9cherry cells were seeded to 15-cm plates, treated with or without 100 ng/ml doxycycline for 7 days, while the medium with or without 100 ng/ml doxycycline was refreshed every 3 to 4 days. On day 7, 2 ml trypsin was added to each plate to detach cells. Cells were collected and counted followed by 3 times PBS washing. Then cells were resuspended by 50% Matrigel (corning #356237) in PBS to make the cell density to be $4 \times 10^6$ cells/100 ul. Cells were then injected to mammary fat pad of nude mice to form tumor. Each injection contains $4 \times 10^6$ cells. Tumor size was measured every 2-3 days.

Figure 3D:
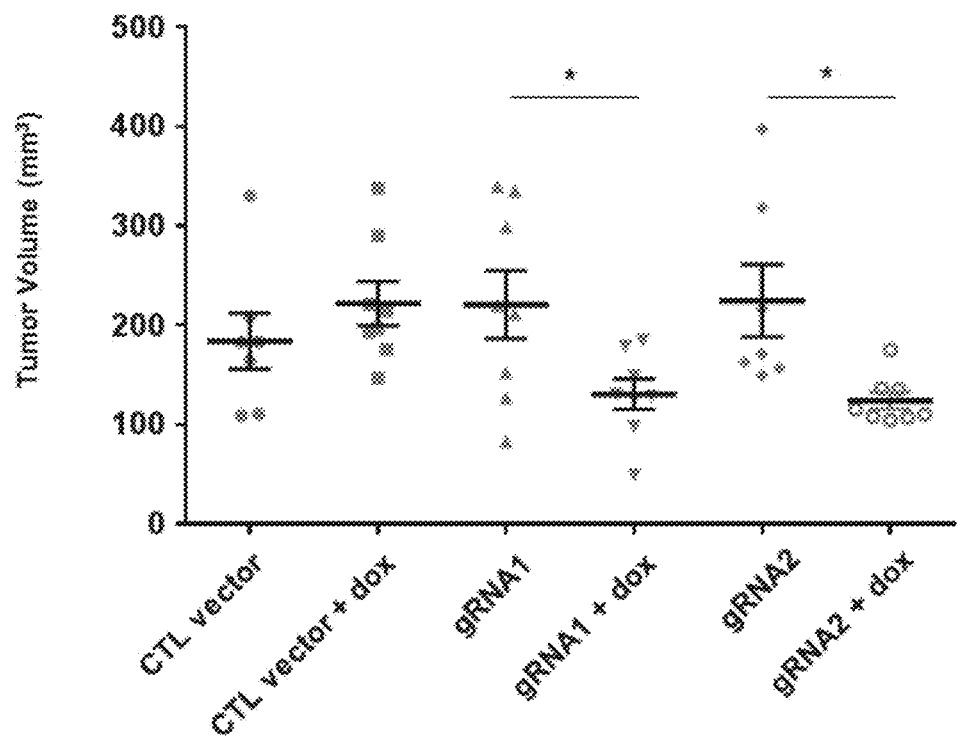
FIG. 3d is a plot showing the volume of tumor on day 9 in xenograft nude mice having transfected HCC1806 cells, in which the HCC1806 cells contain gRNA 1, gRNA 2 or empty vector and were treated with dox for 7 days before injection into mammary fat pad of the nude mice (n=8); *p<0.05.

FIG. 3d shows the gRNA molecule of the present invention together with the induction by the inducible promoter can inhibit the growth and progression of tumor or cancer. The sizes of HCC1806 tumors in the xenograft nude mice significantly reduced compared to the control groups.

CONCLUSION

Upon administration of the inducible promoter, i.e. dox administration, TCOF1 is depleted significantly in cancer cells infected with the two gRNAs of the present invention. As discussed in Example 3, the consequence of TCOF1 knockout on TNBC cell proliferation was investigated in both 2D and 3D cultures. The results demonstrated that depletion of TCOF1 in TNBC line HCC1806 potently inhibits cell proliferation in both 3D and 2D cultures, while the dox administration in vector-control cells has no effect on proliferation. Similar reduction of cell proliferation by TCOF1 depletion is observed in MDA-MB-468 cells as shown in FIG. 4c. Furthermore, TCOF1 knockout potently inhibits colony formation in a clonogenic assay as shown in FIGS. 4d and 4e, demonstrating its critical role in regulating the progeny producing capability of TNBC cells. Importantly, TCOF1 knockout significantly inhibits TNBC growth in the xenograft model as discussed in Example 4. These data show that the gRNA molecules of the present invention are useful to treat and/or prevent TNBC, particularly for tumors and/or cancer cells having elevated expression of TCOF1.

---

The invention claimed is:

1. A gRNA molecule comprising the sequence of SEQ ID NO:1 or SEQ ID NO:2.

2. A kit comprising a recombinant vector which comprises the gRNA molecule of claim 1.

3. The kit of claim 2, wherein the kit further comprises an inducible promoter for inducing the expression of the gRNA molecule in a cell.

4. A method of treating a subject suffering from a breast cancer associated with an elevated expression of TCOF1 gene, the method comprising the step of administering an effective amount of a gRNA molecule comprising the sequence of SEQ ID NO:1 or SEQ ID NO:2, wherein the breast cancer is triple negative breast cancer.

5. The method of claim 4, wherein a second recombinant vector comprising a sequence encoding the Cas9 protein is administered to the subject before, after or simultaneously with the gRNA molecule.

6. A method of inhibiting the expression of TCOF1 gene in cells associated with an elevated expression of TCOF1 gene, the method comprising the step of contacting the cells with a gRNA molecule comprising the sequence of SEQ ID NO:1 or SEQ ID NO:2.

7. The method of claim 6, further comprising the step of contacting the cells with a second recombinant vector comprising a sequence encoding the Cas9 protein before, after or simultaneously with the gRNA molecule.

8. The method of claim 6, wherein the cells are breast cancer cells.

9. The method of claim 6, wherein the cells are triple negative breast cancer cells.

* * * * *